United States Patent [19]

Owen

[11] 4,254,222

[45] Mar. 3, 1981

[54] SEMI-QUANTITATIVE ASSAY OF LACTIC ACID AND β-HYDROXY BUTYRATE

[76] Inventor: Oliver E. Owen, 1401 Spring Mill Rd., Gladwyne, Pa. 19035

[21] Appl. No.: 925,946

[22] Filed: Jul. 19, 1978

[51] Int. Cl.$^3$ .............................................. C12Q 1/32
[52] U.S. Cl. ..................................... 435/26; 435/805; 435/810
[58] Field of Search .................. 195/99, 103.5 R, 127; 422/56, 57, 61; 435/26, 805, 810

[56] References Cited

U.S. PATENT DOCUMENTS

| | | | |
|---|---|---|---|
| 3,528,888 | 9/1970 | Deutsch | 435/26 |
| 3,539,453 | 11/1970 | Deutsch | 435/26 |
| 3,867,258 | 2/1975 | Forgione | 435/26 |

OTHER PUBLICATIONS

Alberti et al., "Rapid Blood Ketone Body Estimation In The Diagnosis Of Diabetic Ketoacidosis", *British Med. J.*, vol. 2, (1972) pp. 565–568.
Babson et al., "A Rapid Colorimetric Assay for Serum Lactic Dehydrogenase", *Clin. Chim Acta*, vol. 12, (1965), pp. 210–215.
Bergmeyer et al., "Colorimetric Assay with L–Lactate, NAD, Phenazine Methasulfate and INT", *Methods of Enzymatic Analysis*, (ed. Bergmeyer) 2nd ed. (1974), pp. 579–582.
Friedland et al., "A Rapid Enzymatic Determination of L (+)-Lactic Acid", *Anal. Biochem.*, vol. 2, (1961), pp. 390–392.
Hochella et al., "Automated Lactic Acid Determination in Serum and Tissue Extracts", *Anal. Biochem*, vol. 10 (1965), pp. 304–317.
Mollering et al., "Visualization of NAD (p)–Dependent Reactions", *Methods of Enzymatic Analysis*, (ed. Bergmeyer) 2nd ed. (1974), pp. 136–144.
Nachlns et al., "The Determination of Lactic Dehydrogenase with a Tetrazolium Salt", *Anal. Biochem*, vol. 1 (1960) pp. 317–326.
Raabo, "Determination of Serum Lactic Dehydrogenase by Tetrazolium Salt Method", *Second J. Clin. and Lab. Investigation*, vol. 15, (1963), pp. 233–238.
Whitaker, "A General Colorimetric Procedure for the Estimation of Enzymes Which are Linked to the NaDH/NAD & System", *Clin. Chim. Acta*, vol. 24 (1969) pp. 23–37.
Zivin, et al., "An Automated Colorimetric Method for the Measurement Of 3–Hydroxy-Butyrate Concentration", *Anal. Biochem.*, vol. 52, (1973), pp. 456–461.

*Primary Examiner*—Thomas G. Wiseman
*Attorney, Agent, or Firm*—Bruce D. Sunstein

[57] ABSTRACT

There is provided a procedure for determining the concentration of a metabolic acid in a biological fluid. The method involves use of a tetrazolium salt, a pyridine nucleotide, an electron carrier, and an enzyme that is a dehydrogenase for the specific acid being assayed. These components are used to form an assay mixture; thereafter a quantity of the fluid to be assayed is combined with the assay mixture, so that there may commence a reaction in which the tetrazolium salt is changed to a formazan in an amount that is indicative of the concentration of the specific acid. In a preferred embodiment, the procedure permits assay of the concentration of beta-hydroxybutyrate, and the assay mixture includes components in the relative proportions of 0.8 micromoles 2-(p-iodophenyl)-3-(p-nitrophenyl)-5-phenyltetrazolium chloride (INT), 0.32 micromoles phenazine methosulfate (PMS), 1.5 micromoles nicotinamide adenine dinucleotide (NAD), and 0.75 International Units beta-hydroxybutyrate dehydrogenase, in a water solution buffered at a pH of approximately 8.5 with hydrogen phosphates of potassium together with glycine and sodium hydroxide and also containing alkylphenoxypolyethyoxyethanol. In another preferred embodiment, the procedure permits assay of lactic acid by means of a similar assay mixture utilizing 27.5 International Units of lactic dehydrogenase in place of the beta-hydroxybutyrate dehydrogenase used in the previously discussed embodiment. In the latter procedure a preferred embodiment of the assay mixture is buffered at a pH of approximately 9.6 in a glycine-sodium hydroxide buffer and also contains phenoxypolyethyoxyethanol.

8 Claims, No Drawings

SEMI-QUANTITATIVE ASSAY OF LACTIC ACID AND β-HYDROXY BUTYRATE

BACKGROUND OF THE INVENTION

The present invention relates to determination of the concentration of specific metabolic acids in biological fluids, and in particular, the concentration of betahydroxybutyrate and lactic acid in biological fluids.

In humans, as well as in certain other animals, the organism may experience or suffer from a state of metabolic acidosis. Of the types of acidosis, there are recognized hyperketonemia, hyperlacticacidemia, uremicacidemia, and toxicacidemia.

On certain occasions, it may be possible to determine that there is present a condition of metabolic acidosis, but determination of the type of acidosis present may be difficult without expensive and time-consuming laboratory analysis. Moreover, it may be difficult to determine even whether there is present a metabolic acidosis condition. For example, with respect to hyperketonemia there is a rapid semi-quantitative test for only one ketone body, namely, acetoacetate. The test for acetoacetate concentration is made by use of a nitroprusside impregnated test surface. The test surface is then immersed in the biological fluid to be assayed, and an indication of the concentration can be obtained by observing the color of the test surface after a predetermined time has elapsed. Disadvantages of the nitroprusside technique are discussed in K. G. M. M. Alberti and T. D. R. Hockaday, "Rapid Blood Ketone Body Estimation in the Diagnosis of Diabetic Ketoacidosis," 1972 British Medical Journal, 2, 565–568. The nitroprusside technique does not measure the concentration of betahydroxybutyrate, the major ketone body. The result is the possibility of a misleading determination of the total ketone bodies in the biological fluids.

Although lactic acidosis may be the most common form of metabolic acidosis, there is a problem in determining rapidly the concentration of lactate in biological fluids. Short of laboratory analysis, it is common for the physician to assume the presence of lactic acidosis when other forms of metabolic acidosis have been ruled out by other techniques. For example, the relatively poor nitroprusside technique is used to rule out the presence of hyperketonemia, and other methods are used to rule out the presence of uremicacidemia and toxicacidemia. Thus, despite the frequency of occurrence of lactic acidosis, the number of cases actually documented on the basis of direct analysis are relatively uncommon.

SUMMARY OF THE INVENTION

It is a primary object of the present invention to provide a rapid semi-quantitative assay for the concentration of a given specific acid in a biological fluid, where the given acid may be, inter alia, beta-hydroxybutyrate or lactic acid.

It is a further object of this invention to provide a method of enzymatic analysis of metabolic acids in a biological fluid.

Another object of this invention is to provide a rapid method of determining the concentration of a metabolic acid in a biological fluid by means of observation of the color of the product of an enzymatic reaction.

Another object of this invention is to provide a method of enzymatic analysis that can be accomplished without recourse to spectrophotometric or colorimetric methods.

It is a further object of this invention to provide an assay mixture, which when combined with a sample of the fluid to be assayed, provides a method of determining metabolic acid concentration by visual inspection.

These and other objects of the invention are achieved by providing a method involving preparation of an assay mixture including a tetrazolium salt, a pyridine nucleotide, an electron carrier, and an enzyme that is a dehydrogenase for the specific acid being assayed. Thereafter, a quantity of the fluid to be assayed is combined with the assay mixture so that there may commence a reaction in which the tetrazolium salt is changed to a formazan in an amount that is indicative of the concentration of the specific acid. There is also provided an assay mixture prepared as heretofore described.

In a preferred embodiment, the method permits assay of the concentration of beta-hydroxybutyrate. In this embodiment, the assay mixture includes components in the relative proportions of 0.8 micromoles 2-(p-iodophenyl)-3-(p-nitrophenyl)-5-phenyl-tetrazolium chloride (INT), 0.32 micromoles phenazine methosulfate (PMS), 1.5 micromoles nicotinamide adenine dinucleotide (NAD), and 0.75 International Units beta-hydroxybutyrate dehydrogenase, in a water solution buffered at a pH of approximately 8.5. The buffering agents include hydrogen-phosphates of potassium together with glycine and sodium hydroxide. The solution also contains alkylphenoxypolyethoxyethanol as the agent to increase solubility of the formazan.

In another preferred embodiment, the method in accordance with the invention permits assay of the concentration of lactic acid in a biological fluid. The method is analogous to that used in connection with beta-hydroxybutyrate, and involves preparation of a similar assay mixture, in which 27.5 International Units of lactic dehydrogenase are utilized in place of the 0.75 International Units of beta-hydroxybutyrate dehydrogenase. The lactic acid assay mixture, in a preferred embodiment, is buffered at a pH of approximately 9.6 in a glycine-sodium hydroxide buffer; alkylphenoxypolyethoxyethanol is also used as the solubilizing agent.

There are also provided assay mixtures for use in practicing the above methods, such mixtures being of a nature heretofore described.

DESCRIPTION OF SPECIFIC EMBODIMENTS

Referring now to a preferred embodiment of the invention relating to a method of assay of the concentration of beta-hydroxybutyrate (BOHB), BOHB is oxidized enzymatically to acetoacetate (AcAc) with a corresponding reduction of nicotinamide adenine dinucleotide (NAD) to NADH.

The NADH that has been formed is ineffective in reducing directly a tetrazolium salt to a formazan. Consequently an intermediate electron carrier is used, in this case phenazine methosulfate (PMS). Reactions then following are the oxidation of NADH back to NAD by PMS, which becomes PMS-H. The reduced PMS-H is then capable of reducing the tetrazolium salt to its formazan. In this embodiment tetrazolium salt used is 2-p-iodophenyl-3-(p-nitrophenyl)-5-phenyltetrazolium chloride (INT).

Accordingly, the reactions in the preferred embodiment of the method for assay of BOHB are as follows:

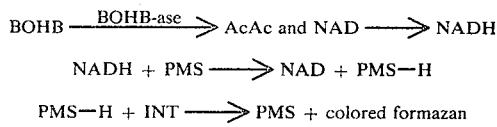

NADH + PMS ⟶ NAD + PMS—H

PMS—H + INT ⟶ PMS + colored formazan

In accordance with this embodiment, there is prepared first a color reagent mixture and a buffer solution. The color reagent mixture consists of a 4 mMolar INT, 1.6 mMolar PMS, and 7.5 mMolar in NAD. To prepare 25 ml of color reagent mixture, one dissolves 50 mg of INT in 20 ml of distilled water, stirring as necessary. When the INT has been completely dissolved, one adds 125 mg NAD and 12.5 mg PMS. When these have been dissolved, one dilutes the mixture with distilled water until the total volume is 25 ml. Preferably, the color reagent should be stored refrigerated in a dark brown bottle or other relatively opaque container, since PMS is sensitive to light.

The buffer solution used in connection with this method is a mixture of two buffer systems. One system is a phosphate buffer employing 0.1 Molar solutions of potassium dihydrogen phosphate and potassium hydrogen phosphate. These solutions are mixed in such proportions as to result in a buffer having a pH of 8.5.

The other buffer system is based on glycine and sodium hydroxide. To this system is also added a small portion of alkylphenoxypolyethyoxyethanol, which is sold under the trademark "Triton X-100" by Rohm and Haas Company, Philadelphia, Pennsylvania. This second buffer system is prepared by dissolving 7.5 g of glycine in 800 ml of distilled water. To this solution is added 20 ml of alkylphenoxypolyethyoxyethanol, whereupon the pH is adjusted to 8.5 with 0.1 Molar sodium hydroxide. The resulting solution is then diluted to 1 liter with distilled water.

After both the phosphate buffer system and the glycine-sodium hydroxide buffer system have been prepared, the combined buffer system is made by mixing the equal volumes of each buffer system.

The BOHB dehydrogenase is in liquid form in concentration of 10 mg/2 ml, 3 I.U./mg.

If desired, concentrated hydrochloric acid diluted with distilled water to 50 percent strength can be prepared for use as described below.

In accordance with a preferred embodiment of the method of the invention, an assay mixture is prepared from the above reagents by mixing in a test tube 0.5 ml of the combined buffer solution, 0.2 ml of the color reagent mixture, and 0.05 ml of BOHB dyhydrogenase in the concentration specified previously. To this assay mixture is then added a 1-drop sample of the biological fluid to be assayed. When 60 seconds have elapsed after the drop has been added, the color of the resulting solution is then observed. If desired, the reaction can be stopped at this point by the addition of the hydrochloric acid solution.

In accordance with the color of the assay solution after 60 seconds of reaction time with the sample, there can be determined the concentration of BOHB in the sample, as set forth in the following table.

| Color Of Solution | Concentration In Sample (mM) |
| --- | --- |
| Faint Yellow | Less than 1 |
| Peach | 2.5 |
| Orange | 5 |
| Red-Orange | 7.5 |
| Brick Red | 10 |

A similar procedure obtains in accordance with a preferred embodiment of the invention for assay of the concentration of lactic acid in a biological fluid. The lactic acid assay involves the enzymatic oxidation of lactic acid to pyruvate with a corresponding reduction of NAD to NADH. The NADH that is formed is oxidized to NAD by PMS, which becomes PMS-H. The reduced PMS-H is then used to reduce INT to its corresponding formazan. The reactions are thus

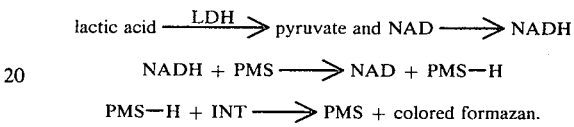

NADH + PMS ⟶ NAD + PMS—H

PMS—H + INT ⟶ PMS + colored formazan.

In accordance with a preferred embodiment of the method employing these reactions, a color reagent mixture is prepared in exactly the fashion described above in connection with BOHB analysis. The buffer solution in this case is, however, entirely a glycine-sodium hydroxide system. Preparation of the buffer is accomplished by dissolving 7.5 g of glycine in 800 ml of distilled water. Thereafter 20 ml of alkylphenoxypolyethyoxyethanol are added, and the pH is adjusted to 9.6 by means of the addition of a water solution of 0.1 Molar sodium hydroxide. The resulting solution is then diluted with distilled water to 1 liter.

The enzyme used in this method is lactic dehydrogenase in a concentration of 25 mg/5 ml, 550 I.U./mg.

Also, as in the case of the BOHB procedure, 50 percent hydrochloric acid may be used as described below.

The assay mixture is prepared by mixing in a test tube 0.5 ml of buffer solution, 0.2 ml of color reagent mixture, and 0.01 ml of lactic dehydrogenase. To the assay solution is added a 1-drop sample of the biological fluid to be assayed, and the reaction product is observed after 60 seconds have elapsed since the reaction was commenced. As in the case of the BOHB procedure, the reaction can be stopped by the addition of the hydrochloric acid mixture.

The concentration of lactic acid can be determined by reference to the same table as is set forth above in connection with BOHB measurement.

It will be understood that numerous other embodiments of the invention are possible. For example, an assay mixture prepared in accordance with one of the above methods may be used to saturate a substance such as paper, and then the water in the solution may be permitted to evaporate. The resulting anhydrous form of the assay mixture impregnated in the paper may permit the paper to be used as a test surface, the color of which, after immersion thereof in a sample to be assayed and a fixed waiting period thereafter, may be an indication of the concentration of the specific metabolic acid being assayed.

Also, for example, the choice of NAD as the pyridine nucleotide is somewhat arbitrary, since nicotinamide adenine dinucleotide phosphate (NADP) has similar properties, although substantially higher concentrations of this pyridine nucleotide would be required, since this enzyme is relatively nonspecific. Furthermore, the use of PMS as the electron carrier is not mandatory. Another electron carrier is 8-dimethylamino-2,3-benzophenoxazine (Meldola Blue), which is in fact less sensitive to light and an efficient carrier. Other possible carriers include diaphorase, thionin, Nile Blue A, and Janus Green B.

Also, the solubilizing agents used for increasing solubility of the formazan are somewhat a matter of choice. Such agents may include gelatin and ethoxylated oleyl alcohol or other non-ionic surface-active agents.

Also, the buffer solutions employed are somewhat a matter of choice, as is the concentrated acid used to stop the reaction.

It may be possible to use tetrazolium salts other than INT, including, for example, 3-(4',5'-dimethylthiazol-2-yl)-2,4-diphenyltetrazolium bromide (MTT).

It will be appreciated that as concentrations of various reagents, and the particular identities of the reagents themselves, are varied, the colors resulting from various concentrations of the metabolic acid being assayed will differ from those presented in the table above. It is significant, however, that various embodiments of the invention will permit a table to be constructed so as to form the basis for the determination of metabolic acid concentration by means of visual inspection of the reaction product of the assay mixture.

Accordingly, while the invention has been described with particular reference to specific embodiments thereof, it will be understood that it may be embodied in a variety of forms diverse from those shown and described without departing from the spirit and scope of the invention as defined by the following claims.

What is claimed is:

1. An assay mixture, for determining the concentration of beta-hydroxybutyrate in a biological fluid, such mixture comprising the following components in the approximate concentrations set forth:

1.1 m Molar tetrazolium salt;
    0.4 m Molar electron carrier;
    2.0 m Molar NAD; and
    1 International Unit/ml beta-hydroxybutyrate dehydrogenase.

2. A mixture according to claim 1, wherein the tetrazolium salt is INT, and the electron carrier is PMS.

3. A mixture according to claim 1, wherein the tetrazolium salt is INT, and the electron carrier is Meldola Blue.

4. The mixture according to any of claims 2 or 3, such mixture further comprising components, in approximate concentrations as follows:
    (i) a mixture of 0.03 Molar potassium dihydrogen phosphate with 0.03 Molar potassium, monohydrogen phosphate in proportions to give in solution a buffer having a pH of approximately 8.5; and
    (ii) 2.5 g. glycine/l, 6.3 ml alkylphenoxypolyethyoxyethanol/l, and sufficient sodium hydroxide to give with the foregoing two components in solution a buffer having a pH of approximately 8.5.

5. An assay mixture for determining the concentration of lactic acid in a biological fluid, such mixture comprising the following components in the approximate concentrations set forth:

1.1 m Molar tetrazolium salt;
    0.45 m Molar electron carrier;
    2.1 m Molar NAD; and
    39 International Units/ml of lactic dehydrogenase.

6. The mixture according to claim 5, wherein the tetrazolium salt is INT, and the electron carrier is PMS.

7. A mixture according to claim 5, wherein the tetrazolium salt is INT and the electron carrier is Meldola Blue.

8. A mixture according to any of claims 6 or 7, such mixture further comprising components in approximate concentrations as follows: 5.3 g glycine/l, 7 ml alkylphenoxylpolyethyoxyethanol/l, and sufficient sodium hydroxide to give with the foregoing two components in solution a buffer having a pH of approximately 9.6.